United States Patent

Kamishita et al.

[11] Patent Number: 5,158,761
[45] Date of Patent: Oct. 27, 1992

[54] SPRAY GEL BASE AND SPRAY GEL PREPARATION USING THEREOF

[75] Inventors: Takuzo Kamishita, Takatsuki; Takashi Miyazaki, Nakaniikawa; Yoshihide Okuno, Namerikawa, all of Japan

[73] Assignee: Toko Yakuhin Kogyo Kabushiki Kaisha, Osaka, Japan

[21] Appl. No.: 496,036

[22] Filed: Mar. 20, 1990

[30] Foreign Application Priority Data

Apr. 5, 1989 [JP] Japan .................................. 1-86339
Jul. 4, 1989 [JP] Japan .................................. 1-172582

[51] Int. Cl.⁵ .............................................. A61L 9/04
[52] U.S. Cl. ........................................ 424/45; 424/89; 424/464; 424/473; 514/772.1
[58] Field of Search ............... 424/45, 89, 78, 473, 424/464

[56] References Cited

U.S. PATENT DOCUMENTS

| | | | |
|---|---|---|---|
| 3,940,351 | 2/1976 | Schlatzer et al. | 524/795 |
| 4,195,076 | 3/1980 | Fontanges | 424/45 |
| 4,267,169 | 5/1981 | Kamishita | 424/78 |
| 4,495,168 | 1/1985 | Schmolka | 424/45 |
| 4,512,972 | 4/1985 | Schmidt-Ruppin | 424/89 |
| 4,625,015 | 11/1986 | Green | 424/89 |
| 4,673,564 | 6/1987 | Kawata | 424/78 |
| 4,717,566 | 1/1988 | Eckenhoff | 424/473 |
| 4,724,210 | 2/1988 | Oka | 424/89 |
| 4,764,382 | 8/1988 | Kydonieus | 424/78 |
| 4,853,430 | 8/1989 | Stühlen | 424/78 |
| 4,883,660 | 11/1989 | Blackman | 424/78 |

FOREIGN PATENT DOCUMENTS

| | | |
|---|---|---|
| 0559001 | 3/1982 | Australia . |
| 1465665 | 2/1977 | United Kingdom . |
| 2007090 | 5/1979 | United Kingdom . |

Primary Examiner—Thurman K. Page
Assistant Examiner—William E. Benston, Jr.
Attorney, Agent, or Firm—Wegner, Cantor, Mueller & Player

[57] ABSTRACT

A spray base gel having an excellent spread-stick property, which is prepared by thickening a 0.2-1.5% by weight aqueous solution of carboxyvinyl polymer with a water-soluble basic substance, followed by adjusting the viscosity thereof with a viscosity adjustor within the range of 500-5,000 centipoise so that the particle size distribution of spray after spraying is over 80% in the area of 20-100 μm and a spray gel preparation having an excellent spread-stick property, which is prepared by mixing an active medicament with said spray gel base.

13 Claims, No Drawings

SPRAY GEL BASE AND SPRAY GEL PREPARATION USING THEREOF

The present invention relates to a gel base suitable for a spray (hereinafter, referred to "spray gel base") and a gel preparation suitable for a spray (hereinafter, referred to "spray gel preparation") which is prepared by mixing said spray gel base with an active medicament uniformly. More particularly, it relates to a spray gel base having an excellent spread-stick property, which is prepared by increasing the viscosity of an aqueous solution of a carboxyvinyl polymer (hereinafter, referred to CVP) with a water-soluble basic substance, and a spray gel preparation which is prepared by mixing said gel base with an active medicament uniformly.

Prior Art

Hitherto, there have been known sprays such as aerosols using hydrocarbon fluoride (e.g. Freon, a trade name of Du Pont) as a propellant, sprays of an aqueous solution of an active medicament using hand-operated pressurization and the like. Among them, aerosols using hydrocarbon fluoride (Freon) as a propellant are not desirable because of the following reasons: that the sprayed active medicament, or powder containing an active medicament, should dissolve on the sprayed spot for exhibiting the pharmacological activity but it is less soluble, and hence, aerosols are inferior to sprays of aqueous solution of an active medicament in exhibiting the pharmacological activity at maximum; and that there are physical stimuli on the sprayed spot due to hydrocarbon fluoride per se and gas spray pressure; and further that hydrocarbon fluoride influences seriously the content of ozone in the stratosphere and has been the subject of restriction on use thereof.

On the other hand, although sprays of aqueous solutions of an active medicament by hand-operated pressurization do not have the defects as described above in aerosols, they have various other defects. That is, sprays of an aqueous solution of an active medicament are bad in spread-stick property, and hence, an aqueous solution of an active medicament drips from the sprayed spot and there is an uncomfortable feeling when it is used, and it is impossible to administer a desired amount of an active medicament to a fixed spot and when an active medicament is water-insoluble, it is also impossible to prepare the preparation containing an active medicament uniformly.

Under the above circumstances, it has been attempted to avoid the liquid dripping by some means, for example, by minimizing the size of a spray nozzle of a nebulizer so that the particle size is smaller when it is sprayed. However, even by such means, the problem of liquid dripping has still not been solved, and it has been sought to develop a means to maintain the desired amount of an active medicament properly at the sprayed spot without liquid dripping.

In order to improve the spread-stick property in sprays of an aqueous solution of an active medicament when it is sprayed, it may be effective to increase the viscosity of said aqueous solution of an active medicament by using conventional water-soluble high molecular weight compounds, which are generally used as thickeners, such as hydroxypropyl cellulose, hydroxypropyl methylcellulose, polyvinyl alcohol, polyvinylpyrrolidone, gelatin, sodium alginate and the like. According to the studies by the present inventors, however, when these conventional thickeners are used, the aqueous solution of an active medicament can not been spurted out of a nebulizer, or even if it can be spurted, the spurted solution is not in the form of mist but becomes like a water column, and hence, the above-mentioned problem is still not solved by such a means.

During intensive study as to a preparation for spraying, the present inventors have found that a gel base prepared by increasing the viscosity of an aqueous solution of CVP with a water-soluble basic substance can be sprayed well by a nebulizer, while the gel base thus obtained has a higher viscosity in comparison with the solution prepared by using the above-mentioned conventional thickeners, and that the liquid dripping can be prevented by using said gel base except when it is applied to a living body. However, the present inventors have found the following defects in said gel base prepared from CVP. That is, the viscosity of the solution of CVP, which is high before spraying, is lowered to some extent by spraying, and when it is applied to a living body such as to a mucous membrane, skin and the like, the viscosity of the solution is rapidly decreased at the sprayed spot so that the solution drips and the desired amount of an active medicament incorporated therein cannot be maintained properly. In order to solve the above-mentioned defects, the present inventors have tried to increase the viscosity of a solution of an active medicament by using CVP at a higher ratio, but in that case, the higher spray pressure was required for spraying it and there was a stimulus due to the high spray pressure at the applied spot. Further, when the solution having such a high viscosity is forced to spray, the particle size of spray becomes extremely big, and when the viscosity of the solution is much higher, it is impossible to spray it.

Under the above-mentioned circumstances, the present inventors have further intensively studied, and as a result, have unexpectedly found that when an aqueous solution containing a comparatively high concentration of a CVP is thickened with a water-soluble basic substance to give a gel having a comparatively high viscosity and then the viscosity thereof is adjusted within the range of 500–5,000 centipoise (cp) with a viscosity adjustor, there can be obtained the desired spray gel base having excellent properties. That is, the spray gel base prepared in the above manner shows little change of viscosity between before and after spraying and shows an excellent spread-stick property, and hence, when it is applied to a living body such as to a mucous membrane or skin, it does not drip from the applied spot. Further, the present inventors have found that a spray gel preparation prepared by mixing the above-mentioned gel base with an active medicament has also extremely excellent properties, and it can release an active medicament constantly to a living body such as to a mucous membrane, skin and the like.

BRIEF DESCRIPTION OF THE INVENTION

An object of the present invention is to provide a spray gel base having excellent spread-stick property and no dripping when applied to a living body which is prepared by thickening the viscosity of an aqueous solution containing a comparatively high concentration of a CVP with a water-soluble basic substance and adjusting the viscosity of the thickened solution to a prescribed range with a viscosity adjustor. Another object of the invention is to provide a spray gel preparation prepared by mixing said gel base uniformly with an active medicament which has excellent absorption of the active medicament when applied to the living body. These objects and other objects and advantages of the invention will be apparent to those skilled in the art from the following description.

DETAILED DESCRIPTION OF THE INVENTION

The present invention provides a spray gel base having an excellent spread-stick property, which is prepared by thickening an aqueous solution containing 0.2-1.5% by weight of CVP with a water-soluble basic substance and adjusting the viscosity thereof within the range of 500-5,000 cp with a viscosity adjustor so that the particle size distribution of spray after spraying is over 80% in the area of 20-100 μm, and further spray gel preparation comprising an active medicament and the spray gel base and having an excellent spread-stick property, which is prepared by thickening an aqueous solution containing 0.2-1.5% by weight of CVP with a water-soluble basic substance, and mixing an active medicament thereto uniformly and then adjusting the viscosity of the mixture within the range of 500-5,000 cp with a viscosity adjustor so that the particle size distribution of spray after spraying is over 80% in the area of 20-100 μm.

Hereinafter, the present invention will be explained in more detail.

CVP used in a spray gel base of the present invention is a hydrophilic polymer which is produced by polymerization of acrylic acid as the main monomer component and includes the conventional one such as Carbopol 934, 934P, 940 and 941 (commercially available from Goodrich, USA). The concentration of CVP aqueous solution used in the present invention is generally in the range of 0.2-1.5% by weight.

A water-soluble basic substance used in the present invention is used for the purpose of thickening CVP aqueous solution to increase the viscosity thereof. A suitable water-soluble basic substance of the present invention includes, for example, inorganic bases (e.g., sodium hydroxide, potassium hydroxide, ammonia, etc.), and organic bases such as alkylamines (e.g., methylamine, ethylamine, propylamine, etc.), dialkylamines (e.g., dimethylamine, diethylamine, dipropylamine, etc.), trialkylamines (e.g., trimethylamine, triethylamine, tripropylamine, etc.), alkanolamines (e.g., methanolamine, ethanolamine, propanolamine, etc.), dialkanolamines (e.g., dimethanolamine, diethanolamine, dipropanolamine, etc.), trialkanolamines (e.g., trimethanolamine, triethanolamine, tripropanolamine, etc.), amino acids (e.g., arginine, lysine, ornithine, etc.) and the like. These water-soluble bases are used in an amount which is necessary for neutralization to adjust the pH value of CVP aqueous solution to the desired pH.

A viscosity adjustor of the present invention is used for the purpose of adjusting the viscosity of a gel which is a comparatively high viscous gel and prepared by thickening the aqueous solution containing 0.2-1.5% by weight of CVP with a water-soluble basic substance, so that the particle size distribution of spray after spraying is over 80% in the area of 20-100 μm. A suitable viscosity adjustor of the present invention includes, for example, sodium chloride, potassium chloride, calcium chloride and the like. It is preferable that the viscosity adjustor of the present invention is used at the ratio of 0.01-10.0% by weight to the total amount of all compositions. Besides, when it is applied to mucous membrane, the amount of a viscosity adjustor should be determined taking into consideration the change of osmotic pressure due to a viscosity adjustor.

It is preferable to adjust the viscosity of a spray gel base of the present invention so that the particle size distribution of spray after spraying is over 80% in the area of 20-100 μm. Only in the case that the particle size distribution of spray after spraying is in the above area, the spray gel base of the present invention has an excellent spread-stick property and the viscosity thereof has not changed between before and after spraying.

A spray gel base of the present invention can be prepared by adding a water-soluble basic substance into the aqueous solution containing 0.2-1.5% by weight of CVP with stirring, and mixing the mixture uniformly to give a viscous gel and adding a viscosity adjustor thereto with stirring to obtain the desired viscosity. When a viscosity adjustor is in a crystal form, it may be added as it is, but it is more preferable to add in the form of an aqueous solution thereof, because when it is added in the form of an aqueous solution, there is no acute change of viscosity, and the viscosity is changed uniformly.

The pH value of a spray gel base of the present invention is adjusted to the desired pH with a water-soluble basic substance or other pH adjustors taking into consideration the stability or absorption of an active medicament.

A spray gel preparation of the present invention can be prepared by thickening an aqueous solution containing 0.2-1.5% by weight of CVP with a water-soluble basic substance and mixing an active medicament therewith uniformly and then adjusting the viscosity of the mixture in the same manner as the above-mentioned spray gel base. Further, depending on the kind of active medicament, a spray gel preparation of the present invention can be prepared by dissolving or dispersing an active medicament in the aqueous solution containing 0.2-1.5% by weight of CVP first, and adding a water-soluble basic substance thereto with stirring and mixing uniformly and then adjusting the viscosity of the mixture in the same manner described above.

Both a water-soluble and water-insoluble medicament can be used as an active medicament of the present invention, but it is more preferable to use medicaments which are stable in a preparation, that is, in an aqueous solvent. A suitable active medicament of the present invention includes, for example, hypnotics and sedatives (e.g., glutethimide, chloral hydrate, nitrazepam, amobarbital, phenobarbital, etc.), antipyretics, analgesics and anti-inflammatory agents (e.g., aspirin, acetaminophen, ibuprofen, flurbiprofen, indomethacin, ketoprophen, dichlofenac sodium, tialamide hydrochloride, piroxicam, flufenamic acid, mefenamic acid, pentazocine, etc.), local anesthetics (e.g., methyl aminobenzoate, lidocaine, etc.), local vasopressors (e.g., naphazoline nitrate, tetrazoline nitrate, oxymethazone hydrochloride, tramazoline hydrochloride, etc.), antiallergic agents (e.g., disodium cromoglycate, oxatomide, azelastine hydrochloride, ketotifen fumarate, traxanox sodium, amlexanox, etc.), cardiotonics (e.g., dopamine hydrochloride, ubidecarenone, etc.), antiarrhythmic drugs (e.g., propranolol hydrochloride, pindrol, phenytoin, disopyramide, etc.), coronary vasodilators (e.g., isosorbide nitrate, nifedipine, diltiazem hydrochloride, dipyridamole, etc.), drugs for digestive organs (e.g., domperidone, etc.), corticosteroids (e.g., triamcinolone acetonide, dexamethasone, betamethasone sodium phosphate, prednisolone acetate, fluocinonide, beclometasone propionate, flunisolide, etc.), antiplasmins (e.g., tranexamic acid, etc.), antifungal agents (e.g., clotrimazole, miconazole nitrate, ketoconazole, etc.), antineoplastic agents (e.g., tegafur, fluorouracil, mercaptopurine, etc.), antibiotics (e.g., amoxicillin, ampicillin, cephalexin, cephalotin sodium, ceftizoxime sodium, erythromycin, oxytetracycline hydrochloride, etc.), biogenic peptides (e.g., insulin, calcitonins such as salmon calcitonin, chicken calcitonin and elcatonin, urokinase, TPA, interferon, etc.), vaccines (e.g., influenza vaccine, pig Bordetella infection preventive vaccine, hepatitis B vaccine, etc.) and the like. The amount of an active medicament used in the spray gel preparation of the present invention varies depending on the kind of medicaments, but an active medicament is usually used in the sufficient amount at which it shows the desired pharmacological activities thereof.

When a water-insoluble medicament is used in the present invention, the spray gel preparation becomes white turbid, but the active medicament does not precipitate, and there is no difficulty for usual administrations. However, in the case that a spray gel preparation of the present invention is applied to skin and the like and the absorption into the living body is better in the form of a solution than in the solid form, it is preferable to prepare the spray gel preparation by using a solubilizer or by dissolving the water-insoluble medicament previously in a water-soluble organic solvent. The suitable water-soluble organic solvent includes, for example, lower alcohols (e.g., ethanol, isopropanol, etc.), glycols (e.g., propylene glycol, 1,3-buthylene glycol, polyethylene glycol having a molecular weight of 300-500, etc.) and the like. The suitable solubilizer is selected from the group consisting of various surfactants, crotamiton, salicylated glycol ester, methyl salicylate, peppermint oil, benzyl alcohol and the like depending on the solubility of an active medicament.

Besides, an active medicament used in the present invention can be suspended by using a suitable suspending agent. A suitable suspending agent includes various surfactants, for example, sucrose fatty acid ester, polyoxyl stearate 40, polyoxyethylene hydrogenated caster oil 60, polysorbate 80, glycerin monostearate, sorbitan monostearate, sorbitan monopalmitate and the like.

It is preferable that the viscosity of the spray gel base and the spray gel preparation of the present invention is adjusted within the range of 500-5,000 cp with a viscosity adjustor such as sodium chloride, potassium chloride, calcium chloride and the like. When the viscosity of the spray gel base or the spray gel preparation of the present invention is below 500 cp, the fluidity thereof is so high that it causes the liquid dripping when it is applied to mucous membrane or to skin. On the other hand, when the viscosity of the spray gel base or the spray gel preparation of the present invention is over 5,000 cp, the particle size of spray after spraying is irregular and big, and hence, it is not suitable for exhibiting the desired effects of the active medicament well. The viscosity of the spray gel base or the spray gel preparation of the present invention is more preferably within the range of 800-3,000 cp.

The spray gel preparation of the present invention can be applied to mucous membranes in nasal cavity, oral cavity, vagina, and the like, and to skins according to the conventional manners. In comparison with the preparations prepared by using the conventional water-soluble high molecular compounds or the CVP gel base or gel preparation prepared without using a viscosity adjustor, the spray gel base and the spray gel preparation of the present invention have more uniform particle size and smaller change of viscosity between before and after spraying thereof, and hence, they are superior in the spread-stick property and they do not drip after spraying.

Moreover, the spray gel preparation of the present invention can be useful in clinical use. For instance, the spray gel preparation of influenza vaccine prepared according to the present invention can be applied to the mucous membrane in the nasal cavity, and it is more desirable than the conventional dosage forms of influenza vaccine.

Hitherto, the influenza vaccine has been inoculated by subcutaneous injection, because the influenza vaccine is a polypeptide having a high molecular weight and hence, the membrane permeability thereof is bad, and it has a tendency to be decomposed in the digestive tracts and it is hardly absorbed into the living body when it is administered orally and further, the inoculation of influenza vaccine is for the purpose of production of anti-virus antibody in blood (humoral immunity).

Essentially, influenza virus causes an infection only on the mucous membrane of the respiratory tract (local infection), and hence, it is more effective to produce an antibody (IgA antibody) on mucous membrane of respiratory tract than to produce an antibody in blood. But, in the conventional subcutaneous inoculation, the mucous membrane of the respiratory tract is not stimulated and hence, secretory IgA cannot be obtained. Further, the subcutaneous inoculation is restricted on use due to side effects thereof and the amount of influenza vaccine which is sufficient for phylaxis cannot be inoculated, and hence, the antibody response level is not adequate and the retention time thereof is short. In addition, influenza virus rages with occurring antigen variation and when the type of antigen in vaccine is different from the type of antigen in raging virus, the preventive effect of the vaccine is decreased.

In order to improve the above-mentioned defects of the conventional dosage forms of influenza vaccine, it has been tried to develop new-style vaccines or dosage forms thereof. Administration into the nasal cavity can be one which induces secretory IgA antibody on the respiratory tract which is an infection route, and is effective for phylaxis.

However, it is difficult to produce secretory IgA on respiratory tract at a high level by spraying influenza vaccine itself or an aqueous solution of influenza vaccine. Because, influenza vaccine is a peptide having a high molecular weight so that the permeability thereof on mucous membrane of respiratory tract is low, and influenza vaccine has difficulty in absorption through the mucous membrane of respiratory tract due to the depuration mechanism of mucous membrane of respiratory tract such as mucous secretion, epithelial abrasion, villus movement and the like.

The nasal spray gel preparation of influenza vaccine of the present invention can be prepared by mixing the spray gel base described above and influenza vaccine. Influenza vaccine used in the present invention may be either attenuated vaccine or inactivated vaccine thereof. When attenuated vaccine is used, it may be either HA vaccine which is prepared by removing lipid components thereof by ether treatment, or virus particle vaccine which is not treated with ether. Further, influenza vaccine used in the present invention includes the new-style vaccines such cold-adapted live vaccine, artificial membrane vaccine, genetic manipulated vaccine, peptide vaccine and the like.

The nasal spray gel preparation of influenza vaccine prepared according to the present invention may contain a suitable active medicament, bactericide, preservative, surfactant, stabilizer and the like which can be used together with influenza vaccine.

The present invention will be illustrated in more detail by the following Experiment, Examples and Preparations, but it should not be construed to be limited thereto. In the following Experiment, Examples and Preparations, the viscosity was determined by C-type Viscosimeter (manufactured by Tokyo Keiki K.K.) at 20° C.

Experiment

The spray tests were carried out in various bases prepared by using the following various thickeners and purified water and the properties of bases were determined in terms of spray condition, rate of viscosity maintenance, spread-stick property, spread-stick property on skin. The results are shown in Table 1.

TABLE 1

| Thickener | Vis. (cp) | Spray condition* | Rate of Vis. M.** | S-S prop. on board (sec)*** | S-S prop. on skin**** |
|---|---|---|---|---|---|
| (Pur. Water) | — | Good | — | 0.71 | Drip |
| HPMC2910 | 2,000 | Bad 1 | — | — | — |
| HPC H | 2,000 | Bad 2 | — | — | — |
| HPC M | 2,000 | Bad 2 | — | — | — |
| PVA | 2,000 | Bad 1 | — | — | — |
| PVP | 2,000 | Bad 1 | — | — | — |
| Gelatin | 2,000 | Bad 1 | — | — | — |
| Sodium Alginate | 2,000 | Bad 2 | — | — | — |
| CVP(0.08%) | 2,000 | Good | 40.4% | 1.55 | Drip |
| CVP(0.2%) | 22,000 | Bad 3 | 41.9% | 30.18 | Drip |
| CVP(0.4%) | 32,000 | Bad 1 | — | — | — |
| CVP(0.4%) + NaCl(0.03%) | 21,000 | Bad 3 | 70.7% | 155.18 | Drip |
| CVP(0.4%) + NaCl(0.27%) | 2,000 | Good | 91.0% | Unchange | Stick |
| CVP(0.6%) | 36,000 | Bad 1 | — | — | — |
| CVP(0.6%) + NaCl(0.22%) | 11,500 | Bad 3 | 72.4% | Unchange | Drip |
| CVP(0.6%) + NaCl(0.45%) | 5,000 | Good | 86.9% | Unchange | Stick |

HPMC: Hydroxypropyl methylcellulose
HPC: Hydroxypropyl cellulose
PVA: Polyvinyl alcohol
PVP: Polyvinylpyrrolidone
*Spray condition was evaluated according to the following standard.
Bad 1: Did not spurt out of a nebulizer.
Bad 2: Spurted out of a nebulizer, the status of the solution was not particle but water column.
Bad 3: Spurted out of a nebulizer, but particles were too big.
Good: Spurted out of a nebulizer uniformly and particles were small.
**Rate of Viscosity Maintenance was estimated according to the following equation.
$$\frac{\text{Viscosity after spraying}}{\text{Viscosity before spraying}} \times 100$$
***The test on the spread-stick property (S-S prop.) was carried out in the following manner. A filter paper No. 6 (diameter: 110 mm) soaked with a physiological saline solution (1.5 g) was stuck on the board inclining at an angle of 40°. From the distance of 30 mm, the content (600 mg) of a nebulizer was sprayed toward the center of the filter paper, and the time (sec.) until the drips started to drop was measured. When drips did not drop, it was evaluated as Unchange.
****The spread-stick property on skin was evaluated in the following manner. The content (180 mg) of a nebulizer was sprayed to the inside part of human upper arm from the distance of 30 mm. When the drips dropped within 10 seconds after spraying, it was evaluated as Drip, and when the drips did not drop for 10 seconds after spraying, it was evaluated as Stick.

As is clear from Table 1, only the gel bases prepared according to the present invention (CVP 0.4% +NaCl 0.27 %, and CVP 0.6% +NaCl 0.45%) are good in all respects such as spray condition, rate of viscosity maintenance, spread-stick properly on both of a board and human skin.

EXAMPLE 1

Preparation of a spray gel of ketoprophen:

The spray gel preparation of ketoprophen was prepared by using the following amount of the components.

| Component | Amount (% by weight) |
|---|---|
| Ketoprophen | 3.0 |
| Polysorbate 80 | 1.0 |
| CVP (4% aqueous solution) | 25.0 |
| Sodium hydroxide (2% aqueous solution) | 20.0 |
| Sodium chloride (10% aqueous solution) | 30.0 |
| Disodium edetate (1% aqueous solution) | 10.0 |
| Purified water | 11.0 |

To 4% aqueous solution of CVP was added 2% aqueous solution of sodium hydroxide gradually with stirring, and the mixture was stirred until it became gel. To this mixture was added 1% aqueous solution of disodium edetate, and then, added a suspension of ketoprophen in polysorbate 80 and purified water gradually and it was stirred uniformly. Further, the viscosity of the mixture was adjusted with 10% aqueous solution of sodium chloride, and the mixture was stirred uniformly and mixed well to give a spray gel preparation of ketoprophen (3%, pH: 6.8, viscosity: 3,800 cp).

EXAMPLE 2

Preparation of a spray gel of tetrazoline nitrate

The spray gel preparation of tetrazoline nitrate was prepared by using the following amount of the components.

| Component | Amount (% by weight) |
|---|---|
| Tetryzoline nitrate | 0.1 |
| CVP (4% aqueous solution) | 17.5 |
| L-Arginine (2% aqueous solution) | 25.0 |
| Sodium chloride (10% aqueous solution) | 7.0 |
| Purified water | 50.4 |

To 4% aqueous solution of CVP was added 2% aqueous solution of L-arginine gradually with stirring, and the mixture was stirred until it became gel. Tetrazoline nitrate dissolved in purified water was added thereto gradually and the mixture was stirred uniformly. Then, the viscosity of the mixture was adjusted with 10% aqueous solution of sodium chloride and the mixture was stirred uniformly and mixed well to give a spray gel preparation of tetrazoline nitrate (0.1%, pH: 5.8, viscosity: 4,500 cp).

EXAMPLE 3

Preparation of a spray gel of disodium cromoglicate

The spray gel preparation of disodium cromoglicate was prepared by using the following amount of the components.

| Component | Amount (% by weight) |
| --- | --- |
| Disodium cromoglicate | 2.0 |
| Conc. glycerin | 1.0 |
| CVP (4% aqueous solution) | 17.5 |
| Sodium hydroxide (2% aqueous solution) | 14.0 |
| Disodium edetate (1% aqueous solution) | 10.0 |
| Sodium chloride (10% aqueous solution) | 2.0 |
| Purified water | 53.5 |

To 4% aqueous solution of CVP was added 2% aqueous solution of sodium hydroxide gradually with stirring, and the mixture was stirred until it became gel. To this mixture was added 1% aqueous solution of disodium edetate, and then, added a solution of sodium cromoglicate in glycerin and purified water gradually and it was stirred uniformly. Further, the viscosity of the mixture was adjusted with 10% aqueous solution of sodium chloride, and the mixture was stirred uniformly and mixed well to give a spray gel preparation of sodium cromoglicate (2%, pH: 6.0, viscosity: 1,500 cp).

EXAMPLE 4

Preparation of a spray gel of oxatomide

The spray gel preparation of oxatomide was prepared by using the following amount of the components.

| Component | Amount (% by weight) |
|---|---|
| Oxatomide | 0.01 |
| Polysorbate 80 | 0.003 |
| CVP (4% aqueous solution) | 10.0 |
| L-Arginine (2% aqueous solution) | 7.5 |
| Sodium chloride (10% aqueous solution) | 3.0 |
| Purified water | 79.487 |

To 4% aqueous solution of CVP was added 2% aqueous solution of L-arginine gradually with stirring, and the mixture was stirred until it became gel. To this mixture were added a suspension of oxatomide in polysorbate 80 and purified water gradually and it was stirred uniformly. Further, the viscosity of the mixture was adjusted with 10% aqueous solution of sodium chloride, and the mixture was stirred uniformly and mixed well to give a spray gel preparation of oxatomide (0.01%, pH: 5.1, viscosity: 1,500 cp).

EXAMPLE 5

Preparation of a spray gel of beclometasone propionate

The spray gel preparation of beclometasone propionate was prepared by using the following amount of the components.

| Component | Amount (% by weight) |
|---|---|
| Beclometasone propionate | 0.1 |
| Polysorbate 80 | 0.01 |
| Conc. glycerin | 1.0 |
| CVP (4% aqueous solution) | 15.0 |
| Sodium hydroxide (2% aqueous solution) | 10.0 |
| Sodium chloride (10% aqueous solution) | 8.0 |
| Purified water | 65.89 |

To 4% aqueous solution of CVP was added 2% aqueous solution of sodium hydroxide gradually with stirring, and the mixture was stirred until it became gel. To this mixture were added a suspension of beclometasone propionate in polysorbate 80, conc. glycerin and purified water gradually and it was stirred uniformly. Further, the viscosity of the mixture was adjusted with 10% aqueous solution of sodium chloride, and the mixture was stirred uniformly and mixed well to give a spray gel preparation of beclometasone propionate (0.1%, pH: 6.0, viscosity: 2,500 cp).

EXAMPLE 6

Preparation of a spray gel of fulnisolide

The spray gel preparation of fulnisolide was prepared by using the following amount of the components.

| Component | Amount (% by weight) |
|---|---|
| Fulnisolide.½ $H_2O$ | 0.0255 |
| Polysorbate 80 | 1.0 |
| Polyethylene glycol 400 | 3.0 |
| CVP (4% aqueous solution) | 15.0 |
| Sodium hydroxide (2% aqueous solution) | 6.0 |
| Sodium chloride (10% aqueous solution) | 4.0 |
| Disodium edetate (1% aqueous solution) | 10.0 |
| Benzalkonium chloride (0.1% aqueous solution) | 10.0 |
| Purified water | 50.9745 |

To 4% aqueous solution of CVP was added 2% aqueous solution of sodium hydroxide gradually with stirring, and the mixture was stirred until it became gel. To this mixture were added 1% aqueous solution of disodium edetate and 0.1% aqueous solution of benzalkonium chloride, and then, added a solution of fulnisolide in polysorbate 80, polyethylene glycol and purified water gradually and it was stirred uniformly. Further, the viscosity of the mixture was adjusted with 10% aqueous solution of sodium chloride, and the mixture was stirred uniformly and mixed well to give a spray gel preparation of fulnisolide (0.0255%, pH: 5.1, viscosity: 2,200 cp).

EXAMPLE 7

Preparation of a spray gel of insulin

The spray gel preparation of insulin was prepared by using the following amount of the components.

| Component | Amount (% by weight) |
|---|---|
| Insulin | 0.1887 |
| CVP (4% aqueous solution) | 5.0 |
| L-Arginine (4% aqueous solution) | 10.0 |
| Sodium chloride (10% aqueous solution) | 0.6 |
| Purified water | 84.2113 |

To 4% aqueous solution of CVP was added 4% aqueous solution of L-arginine gradually with stirring, and the mixture was stirred until it became gel. To this mixture was added a solution of insulin in purified water gradually and it was stirred uniformly. Further, the viscosity of the mixture was adjusted with 10% aqueous solution of sodium chloride, and the mixture was stirred uniformly and mixed well to give a spray gel preparation of insulin (50 U/g, pH: 7.3, viscosity: 550 cp).

EXAMPLE 8

Preparation of a nasal spray gel of influenza HA vaccine

The nasal spray gel preparation of influenza HA vaccine was prepared by using the following amount of the components.

| Component | Amount (% by weight) |
| --- | --- |
| Influenza HA vaccine (A/Yamagata/120/86) in phosphate buffer (830 μg protein/ml) | 30.0 |
| CVP (4% aqueous solution) | 15.0 |
| L-Arginine (4% aqueous solution) | 33.8 |
| Sodium chloride | 0.9 |
| Purified water | 20.3 |

To 4% aqueous solution of CVP was added 4% aqueous solution of L-arginine gradually with stirring, and the mixture was stirred until it became gel. To the mixture was added a solution of influenza HA vaccine in phosphate buffer gradually and it was stirred uniformly. Further, the viscosity of the mixture was adjusted with a solution of sodium chloride in purified water, and the mixture was stirred uniformly and mixed well to give a nasal spray gel preparation of influenza HA vaccine (249 μg protein/ml, pH: 7.2, viscosity: 2,900 cp).

EXAMPLES 9-11

The nasal spray gel preparations of influenza HA vaccine (A/Yamagata/120/86) were prepared by using the following amount of the components in Table 2.

TABLE 2

| Component | Ex. 9 | Ex. 10 | Ex. 11 |
|---|---|---|---|
| Influenza HA vaccine in phosphate buffer* | 50 | 50 | 50 |
| CVP (4% aq. sol.) | 15 | 15 | 15 |
| L-Arginine (8% aq. sol.) | 16.9 | 16.9 | 16.9 |
| Sodium chloride | 0.9 | 0.85 | 0.63 |
| Purified water | 17.2 | 17.25 | 17.47 |
| pH | 7.3 | 7.3 | 7.3 |
| Viscosity (cp) | 2,500 | 2,900 | 4,000 |

*A/Yamagata/120/86, 500 μg protein/ml

To 4% aqueous solution of CVP was added 8% aqueous solution of L-arginine gradually with stirring, and the mixture was stirred until it became gel. To this mixture was added a solution of sodium chloride in purified water gradually and it was stirred uniformly and mixed well to give a spray gel base. Further, the spray gel thus obtained was subjected to high-pressure steam sterilization (121° C., 20 minutes) and then mixed uniformly with influenza HA vaccine solution (500 μg protein/ml) which was concentrated under aseptic condition to give a nasal spray gel preparation of influenza HA vaccine.

REFERENCE EXAMPLE 1

Influenza HA vaccine (A/Yamagata/120/86) was dissolved in phosphate buffer (pH: 7.4) to give a nasal spray preparation of influenza HA vaccine (249 μg protein/ml).

REFERENCE EXAMPLE 2

Influenza HA vaccine (A/Yamagata/120/86) was dissolved in phosphate buffer (pH: 7.3) to give a nasal spray preparation of influenza HA vaccine (250 μg protein/ml).

Pharmacological Test

Using the nasal spray gel preparations of influenza HA vaccine prepared in Examples 8-11 and the nasal spray preparations of influenza HA vaccine prepared in Reference Examples 1 and 2, the following pharmacological tests were carried out.

[Method]

(1) Method of immunization:

BALB/C mice were anesthetized by intraperitoneal injection of Nembutal injection (sodium pentobarbiturate, diluted 15-folds)(0.2–0.3 ml/mouse). Holding the anesthetized BALB/C mice, the nasal cavity thereof was turned up and then the preparation (20 μl/mouse) was administered into one of the nasal cavities.

(2) Method of sampling:

The serum for determination of the hemagglutination-inhibition antibody value (abbreviated as HI antibody value) was collected from the mice at 3 weeks after immunization (all bleed was taken out), and breast thereof was cut open and the trachea was exposed. From the top point of the trachea under the chin, a diluted solution of anti IgA antibody (1 ml) was injected into the trachea toward the lungs, and sucked mildly. By repeating the suction and injection, the samples were collected.

(3) Method of determination of HI antibody value:

Serum sample (0.1 ml) was treated with a receptor destroying enzyme (RED) (neuraminidase, 0.3 ml), and kept at 37° C. overnight and then immobilized by treating at 56° C. for 1 hour. A drop of chicken erythrocytes was added thereto, and the mixture was shaken and allowed to stand at room temperature for 1 hour and then the supernatant was collected by centrifuge (2,000 rpm ×10 min.).

The amount of antigen of the strain used in the assay was adjusted to 16 HA. Each of phosphate buffer (0.025 ml) was put into 96 wells of a microplate except for the first one. Test sample (0.05 ml) was put into the first well. Samples in all wells were diluted by an autodiluter. A solution of antigen (0.025 ml) of which amount was adjusted to 16 HA was put into all wells of the microplate, and the plate was well shaken by a plate mixer and allowed to stand for 1 hour. After adding 0.5% blood cells (0.05 ml) to all wells, the plate was again shaken and allowed to stand for 1 hour, and the figure at each well bottom was observed.

(4) Method of IgA assay:

Using Dynatech Immulon II Flatbottom Plates, HANA antigen, which was diluted with 0.05M bicarbonate buffer (pH: 9.5) to the optimum concentration (about 1–10 μg/ml), was put into each well of the said plate in an amount of 100 μl. The plate was allowed to stand at 4° C. overnight (about for 18 hours). On the next day, the plate was washed with 0.01 M phosphate buffer (pH: 7.2) containing 0.05% Tween 20 three times, and then, it was subjected to blocking by treating with phosphate buffer containing 0.1% BSA (bovine serum albumin) at 37° C. for 1 hour to give an antigen solid phase. A control plate was prepared in the same manner as described above except for using seroliquidurine instead of HANA antigen.

Each 100 μl of a diluent for sample (0.01 M phosphate buffer containing 0.5% BSA and 0.05% Tween 20) was put into each well of the plate and thereto added 10 μl of sample. The plate was wrapped with Saran Wrap (polyvinylidene chloride film) and reacted at 4° C. overnight. On the next day, the reaction mixture in each well was removed by suction, and further the wells were washed with a washing fluid (0.01 M phosphate buffer containing 0.05% Tween 20) three times.

A labelled antibody (peroxidase labelled anti-mouse IgA antibody) was diluted to the optimum concentration with the same diluent for sample as above and put into the wells of the plate in an amount of 100 μl. The plate was reacted at room temperature for 2 hours and then washed with the above-mentioned washing fluid three times.

Each 100 μl of a substrate solution (0.1 M citrate buffer, pH: 4.9, containing 3.3 mg/ml o-phenylenediamine, 0.02% $H_2O_2$) was put into the wells and reacted at room temperature under light-shading for 0.5-1.0 hour, and then, the reaction was quenched by adding 1.5 N sulfuric acid (100 μl). The absorbance (492 nm) was determined with an autoreader for microplate.

(5) Results:

The results were shown in the following Table 3.

TABLE 3

|  | IgA antibody | HI antibody value in blood |
| --- | --- | --- |
| Example 8 | 1.35 | 512 |
| Example 9 | 0.342 | 512 |
| Example 10 | 0.531 | 512 |
| Example 11 | 0.284 | 256 |
| Ref. Ex. 1 | <0.001 | 64 |
| Ref. Ex. 2 | <0.001 | <16 |

As is clear from the above results, in the mice to which the nasal spray gel preparation of influenza HA vaccine prepared according to the present invention was administered, anti-virus IgA antibody was detected in the nasal washings at 3 weeks after administration, and HI antibody was also detected at the high level in blood. On the contrary, in the mice to which the solution of influenza HA vaccine in phosphate buffer (Reference Examples 1 and 2) was administered, IgA antibody was little detected and HI antibody in blood was detected only at the low level under the same conditions.

What is claimed is:

1. A gel preparation for spray into a nasal cavity comprising an aqueous gel of a carboxyvinyl polymer having a viscosity of 500-5,000 centipoise and pH 4-9, which is prepared by thickening a 0.2-1.5% by weight aqueous solution of carboxyvinyl polymer with a water-soluble basic substance selected from the group consisting of sodium hydroxide, potassium hydroxide, ammonia, alkylamines, dialkylamines, trialkylamines, alkanolamines, dialkanolamines, trialkanolamines, and amino acids in an amount which is necessary for neutralization to adjust the pH value of the aqueous solution of carboxyvinyl polymer to pH 4-9, followed by adjusting the viscosity within the range of 500-5,000 centipoise, and an effective amount of an influenza vaccine selected from the group consisting of virus particle vaccine, HA vaccine, live virus vaccine, artificial membrane vaccine, genetic manipulated vaccine and peptide vaccine.

2. A method of delivering a medicament by spraying into the nasal cavity which comprises:

adding an effective amount of an influenza vaccine selected from the group consisting of virus particle vaccine, HA vaccine, live virus vaccine, artificial membrane vaccine, genetic manipulated vaccine and peptide vaccine to a gel base for spray to form a gel preparation, wherein said gel base comprises an aqueous gel of a carboxyvinyl polymer having a viscosity of 500-5,000 centipoise and pH 4-9, which is prepared by thickening a 0.2-1.5% by weight aqueous solution of carboxyvinyl polymer with a water-soluble basic substance selected from the group consisting of sodium hydroxide, potassium hydroxide, ammonia, alkylamines, dialkylamines, trialkylamines, alkanolamines, dialkanolamines, trialkanolamines, and amino acids in an amount which is necessary for neutralization to adjust the pH value of the aqueous solution of carboxyvinyl polymer to pH 4-9, followed by adjusting the viscosity thereof with a viscosity adjustor selected from the group consisting of sodium chloride, potassium chloride and calcium chlorine in an amount which is necessary for adjusting the viscosity within the range of 500-5,000 centipoise, and administering said gel preparation to a subject in need an effective amount of an influenza vaccine selected from the thereof by spraying into a nasal cavity.

3. The method according to claim 2, wherein said influenza vaccine is dissolved by adding a solubilizer or with solvent.

4. The method according to claim 2, wherein said influenza vaccine is suspended by adding a suspending agent.

5. The method according to claim 2, wherein the gel preparation has a pH of 6.0-8.0.

6. The gel preparation according to claim 1, which is for application to mucous membrane or skin.

7. The gel preparation according to claim 1, wherein the influenza vaccine is dissolved by adding a solubilizer or with a solvent.

8. The gel preparation according to claim 1, wherein the influenza vaccine is suspended by adding a suspending agent.

9. The gel preparation according to claim 1, which has a pH value within the range of 6.0-8.0.

10. The gel preparation according to claim 6, wherein the influenza vaccine is dissolved by adding a solubilizer or with a solvent.

11. The gel preparation according to claim 6, wherein the influenza vaccine is suspended by adding a suspending agent.

12. The method according to claim 2, wherein said gel preparation is applied to mucous membrane or skin.

13. The method according to claim 2, wherein the gel preparation is sprayed into a nasal cavity.

* * * * *